United States Patent
Shao et al.

(10) Patent No.: US 9,416,359 B2
(45) Date of Patent: Aug. 16, 2016

(54) METHOD FOR CONSTRUCTING MUTAGENESIS LIBRARIES IN SITU

(76) Inventors: Weilan Shao, Nanjing (CN); Yilin Le, Nanjing (CN); Jianjun Pei, Nanjing (CN)

(*) Notice: Subject to any disclaimer, the term of this patent is extended or adjusted under 35 U.S.C. 154(b) by 172 days.

(21) Appl. No.: 13/254,859

(22) PCT Filed: Mar. 15, 2010

(86) PCT No.: PCT/US2010/027364
§ 371 (c)(1),
(2), (4) Date: Sep. 6, 2011

(87) PCT Pub. No.: WO2010/105276
PCT Pub. Date: Sep. 16, 2010

(65) Prior Publication Data
US 2012/0004142 A1    Jan. 5, 2012

(51) Int. Cl.
*C12N 15/10* (2006.01)
*C12N 15/64* (2006.01)
*C40B 40/08* (2006.01)
*C40B 50/06* (2006.01)

(52) U.S. Cl.
CPC ............ *C12N 15/1093* (2013.01); *C12N 15/10* (2013.01); *C12N 15/102* (2013.01); *C12N 15/64* (2013.01); *C40B 40/08* (2013.01); *C40B 50/06* (2013.01)

(58) Field of Classification Search
None
See application file for complete search history.

(56) References Cited

U.S. PATENT DOCUMENTS

2003/0044980 A1* 3/2003 Mancebo et al. ............ 435/455
2004/0023327 A1* 2/2004 Short et al. .................. 435/69.1

FOREIGN PATENT DOCUMENTS

WO    WO2010003659    * 1/2010

OTHER PUBLICATIONS

Miyazaki et al in "Creating Random Mutagenesis Libraries Using Megaprimer PCR of Whole Plasmid" (Biotechniques, Nov. 2002:vol. 33, No. 5, pp. 1033-1038.*
Bichet et al. Applied biochemistry and biotechnology 117.2 (2004): 115-122.*

* cited by examiner

*Primary Examiner* — Heather Calamita
*Assistant Examiner* — Sahana Kaup
(74) *Attorney, Agent, or Firm* — Kening Li; Miller Canfield

(57) ABSTRACT

Method and kit for constructing a random mutagenesis library. The method comprises providing a first expression vector comprising a target polynucleotide fragment, providing a pair of Vector-primers that are complementary to the vector portion of the first expression vector, wherein the Vector-primers comprise a second selection marker gene, and wherein the Vector-primers allow PCR amplification of the target polynucleotide; and performing a PCR reaction using the first expression vector as the template with the Vector-primers under error-prone PCR conditions in the presence of a thermostable DNA ligase, generating a second expression vector which comprises the second selection marker gene and a mutated target polynucleotide.

20 Claims, 4 Drawing Sheets

METHOD FOR CONSTRUCTING MUTAGENESIS LIBRARIES IN SITU

BACKGROUND OF THE INVENTION

1. Field of the Invention

The present invention relates generally to protein and genetic engineering, and more specifically to a method for in situ construction of mutagenesis libraries and kits used therefor.

2. Description of the Related Art

Directed evolution methods are increasingly used on industrial enzymes to improve the enzymes' substrate specificity, activity, thermostability, and high-temperature activity etc. (1-4). The success of directed protein evolution experiments hinges on the efficiency of methods used to create random mutagenesis libraries and screen libraries for mutants with properties of interest (5). Because library diversity represents a crucial parameter in directed evolution of a target gene for improved functionality, various protocols have been established for creating random mutagenesis libraries (6). Random mutagenesis, along with genetic selection or high-throughput screening (5), constitutes an important approach to identifying critical regions of proteins, studying structure-function relations and developing novel proteins with desired properties.

Many methods for directed evolution of enzymes were reviewed by Lutz and Patrick (7); and some of the more recent in vitro DNA mutagenesis approaches were described in both polymerase chain reaction (PCR) and non-PCR categories (8). One of the most commonly used random mutagenesis methods is error-prone PCR (9), which introduces random mutations during PCR by reducing the fidelity of the DNA polymerase. The natural error rate of the polymerase can be altered and enhanced by modifying the standard PCR methods (10). This technique has the advantage of developing new enzymatic properties without a structural understanding of the targeted enzyme, and often yields unique mutations that could not be predicted (10). Early techniques of error-prone PCR generally involves the following steps: 1) amplifying the target gene as the PCR template under error-prone conditions, to generate amplified target sequence that contain random mutations; 2) treating the terminal of the amplified target sequences using restriction endonucleases; 3) ligating the treated target sequence into a suitable expression vector using a DNA ligase; and 4) transforming the expression vector containing the target sequences into a suitable host cell, to obtain a population of cells, or mutagenesis library, which contain the various target sequences. This process is similar to a cloning or subcloning process of the target sequence, except that in conventional cloning or subcloning, only a small number of transformants need to be obtained, while in the construction of a mutagenesis library, generally tens of thousands of transformants are needed in order to realistically be able to obtain a suitable target mutant. This is a tedious and inefficient process.

In order to improve efficiency, a method of PCR amplification of whole plasmid using mega-primer, referred to as "MEGAWHOP" was devised for generating random mutagenesis libraries (11). This process effectively modifies steps 2 and 3 of the above process, and uses randomly mutagenesized target sequence as PCR primers, expression vector as the template, and high-fidelity DNA polymerase. Amplification products are treated with Dpn I, which degrades the template expression vector, but leaves intact the amplified product. The process yields double-stranded full-strength plasmid, avoiding the steps of restriction enzyme treatment and ligation. This method yields libraries that are virtually free of plasmid containing no or multiple inserts. The mega-primer-based PCR method has been improved greatly since it was originally developed (12-15).

Nevertheless, the mega-primer-based PCR method has its own drawbacks. For example, the mutated target sequences have to be specifically synthesized for each target sequence. Further, for the process to be somehow satisfactory, the size of the megaprimers should be in the range of between 500 to 1000 bases, thereby limiting the size of the target sequence. The amplification products using the mega primers are linear sequences, which is not amenable to forming a circular plasmid having two nicks, resulting in relatively low transformation efficiency. Furthermore, the method of mutagenizing the megaprimers also involves a restriction enzyme digestion of the PCR product and of the expression vector, making the process complicated and low in efficiency.

Therefore, there is a need for a faster, simpler and more universally applicable method for generating random mutagenesis libraries.

SUMMARY OF THE INVENTION

The present invention satisfies the above needs by providing a method of constructing a mutagenesis library by error-prone PCR in the presence of a thermally stable DNA ligase (e.g. that from the hyperthermophilic bacterium *Thermotoga maritima* (16)), with a pair of primers that comprise an antibiotic-resistance gene using the whole plasmid as template.

In one embodiment, the present invention provides a method of constructing a random mutagenesis library, comprising i) providing a first expression vector comprising a target polynucleotide fragment, wherein the first expression vector comprises a vector portion and a target portion, wherein the vector portion comprises a first selection marker gene, and a first region and a second region flanking the first selection marker gene, wherein the target portion comprises a target polynucleotide capable of being expressed; ii) providing a pair of Vector-primers that are complementary to the vector portion of the first expression vector in the first and second regions, wherein the Vector-primers comprise a second selection marker gene, and wherein the Vector-primers allow PCR amplification of the target polynucleotide; and iii) performing a PCR reaction using the first expression vector as the template with the Vector-primers under error-prone PCR conditions in the presence of a thermostable DNA ligase, generating a second expression vector which comprises the second selection marker gene and a mutated target polynucleotide. Preferably, the first expression vector has been confirmed to express the target polynucleotide.

In another embodiment, the second expression vector is transformed into a suitable host cell, which is further cultured to allow the second selection marker gene to be expressed for selection of the second expression vector. The host cell comprising the second expression vector may preferably be cultured under a condition to allow the expression of the mutated target polynucleotide. In one embodiment, the first selection marker gene is a first antibiotic resistance gene, and the second selection marker gene is a second antibiotic gene.

In another embodiment of the method according to the present invention, the expression product of the mutated polynucleotide is assayed to select a mutated target polynucleotide with one or more desired mutations. This can be done, for example by assaying or analyzing the phenotype of the mutated gene.

The method of the present invention can be repeated, that is, the expression vector selected in accordance to the steps above, comprising a mutated target polynucleotide with one or more desired mutations, is used as template and subject to further mutation, selection and directed evolution. For example, the expression vector comprising a mutated target polynucleotide with one or more desired mutations is used as a template in a PCR under error-prone conditions with a second pair of Vector-primers that are complementary to the vector portion of the expression vector comprising the desired mutated polynucleotide, wherein the second pair of Vector-primers comprise a third selection marker gene, and wherein the second Vector-primers allow PCR amplification of the target polynucleotide. A PCR reaction with the second Vector-primers is performed under error-prone PCR conditions in the presence of a thermostable DNA ligase, generating a third expression vector which comprises the third selection marker gene and a further mutated target polynucleotide.

In embodiments of the present invention, the third selection marker may be the same as the first selection marker.

In another embodiment, the present invention provides a method of constructing a random mutagenesis library, comprising i) providing a first expression vector comprising a target polynucleotide fragment, wherein the first expression vector comprises a vector portion and a target portion, wherein the vector portion comprises a first selection marker gene, and a first region and a second region flanking the first selection marker gene, wherein the target portion comprises a target polynucleotide capable of being expressed; ii) providing a pair of Vector-primers that are complementary to the vector portion of the first expression vector in the first and second regions, and complementary to a portion of the target polynucleotide that is not desired to be mutated, wherein the Vector-primers comprise a second selection marker gene, and wherein the Vector-primers allow PCR amplification of the target polynucleotide; and iii) performing a PCR reaction using the first expression vector as the template with the Vector-primers under error-prone PCR conditions in the presence of a thermostable DNA ligase, generating a second expression vector which comprises the second selection marker gene and a mutated target polynucleotide.

In one embodiment, a second expression is provided, the target nucleotide sequence is cloned into the second expression vector to result in a Plasmid 2, wherein a pair of PCR primers are designed to amply the entire Plasmid 2 except the portion of the target polynucleotide that is not desired to be mutated under high-fidelity PCR conditions, resulting in the Vector-primers that allows PCR amplification of the target polynucleotide only. The second expression vector may be transformed into a suitable host cell, which is further cultured to allow the second selection marker gene to be expressed for selection of the second expression vector.

In another embodiment, the expression vector comprising a mutated target polynucleotide with one or more desired mutations is used as a template in a PCR under error-prone conditions with a second pair of Vector-primers that are complementary to the vector portion of the expression vector comprising the desired mutated polynucleotide, wherein the the second pair of Vector-primers that comprise a third selection marker gene, and wherein the second Vector-primers allow PCR amplification of the target polynucleotide; and performing a PCR reaction with the second Vector-primers under error-prone PCR conditions in the presence of a thermostable DNA ligase, generating a third expression vector which comprises the third selection marker gene and a further mutated target polynucleotide.

The present invention further provides a kit comprising in a container, an expression vector comprising a first selection marker, and a Vector-primers which comprises a second selection marker flanked by a first and second regions which first and second regions are complementary to the corresponding regions of the first selection marker of the expression vector.

The kit may further comprise a thermostable DNA ligase, such as the ligase from *Thermotoga maritima*.

BRIEF DESCRIPTION OF THE DRAWINGS

For exemplification purposes, and not for limitation purposes, embodiments of the invention are illustrated in the figures of the accompanying drawings, in which:

FIG. 2 illustrates three examples: 1) a target nucleotide sequence comprising three segments, only the middle of which is to be mutated; 2) a shuttle vector, only the second replicon of which is to be mutated; and 3) a construct comprising a regulatory region, an operon, and a reporter gene, wherein only the regulatory region is to be mutated.

FIG. 3 is another depiction of a method for creating random mutagenesis libraries according to the present invention: a.

PCR of the first vector comprising the target polynucleotide sequence using a Vector-primer comprising a second selection marker (i.e. kanamycin resistance gene kan'): denaturing, annealing and enzymatic extension, ligation of the nicked circular plasmid; b. transformation of PCR products into a suitable host cell, and expression of the selection marker gene, followed by selection of mutants with desired mutation/directional evolution. Optionally, this step is repeated, wherein a second megaprimer/PRIMECTOR, comprising a third selection marker (which may be the same as the same as the first selection marker, as illustrated herein, i.e. ampicilin resistance gene, amp'). These are illustrated as Steps c through d.

Figure 4:
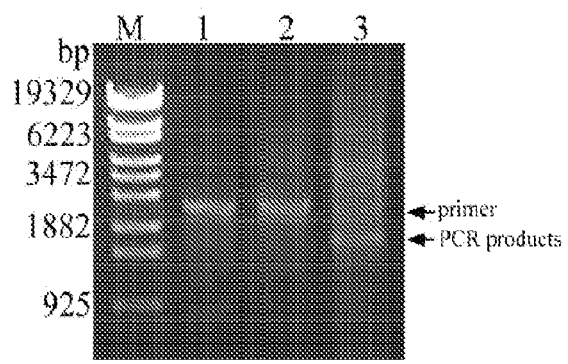

FIG. 4 shows the agarose gel electrophoresis of the PCR reaction with pHsh-xynA1 as template. Lane M, λ EcoT14 I marker; Lane 1, Control, PCR reaction (no Taq DNA polymerase and DNA ligase); Lane 2, Control, PCR reaction using Taq DNA polymerase; Lane 3, PCR reaction using Taq DNA polymerase and thermostable DNA ligase.

Figure 5:
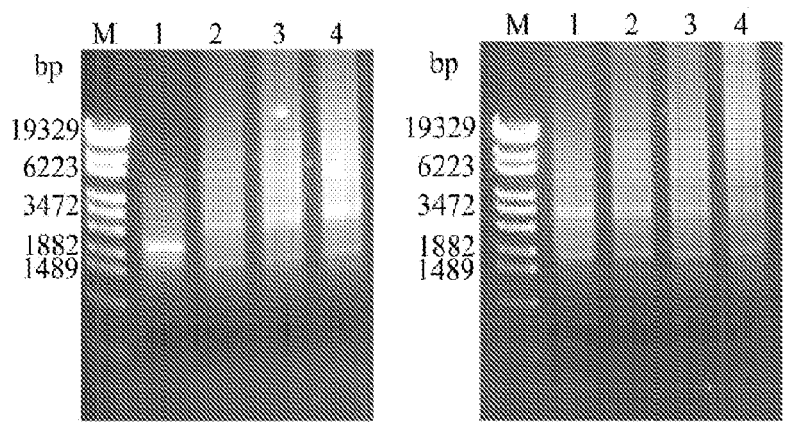

FIG. 5 shows the effects of 60° C. ligation time and 72° C. anneal time on PCR. (A) Effects of 60° C. ligation time on PCR were performed in a 20 µl reaction system. Lane M, λ EcoT14 I marker; Lane 1, 0 min; Lane 2, 1 min; Lane 3, 2 min; Lane 4, 3 min. (B) The effect of 72° C. anneal time on PCR were performed in a 20 µl reaction system. Lane M, λ EcoT14 I marker; Lane 1, Control (0 min); Lane 2, 1 min; Lane 3, 2 min; Lane 4, 3 min.

Figure 6:
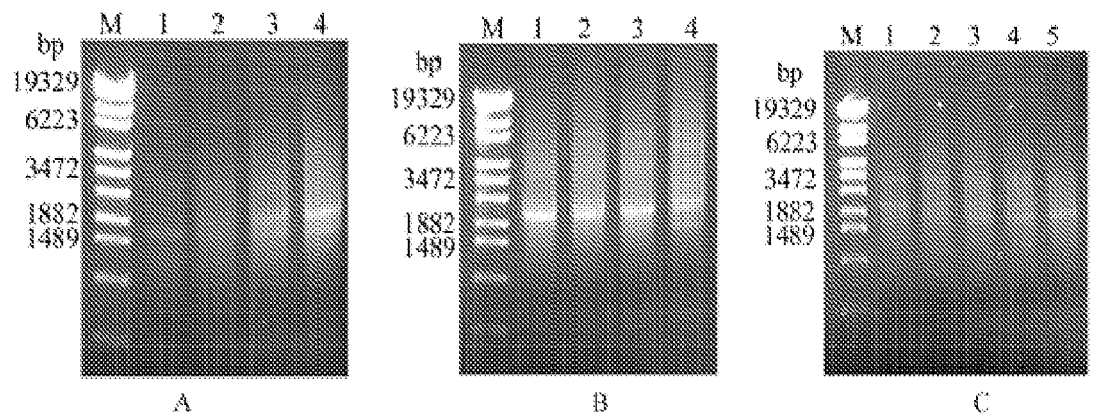

FIG. 6 shows the effects of amounts of Vector-primers, plasmid template and DNA ligase on PCR reaction. (A) The effect of Vector-primers amounts on PCR was performed in a 20 µl reaction system. Lane M, λ EcoT14 I marker; Lane 1,100 ng; Lane 2, 150 ng; Lane 3, 200 ng; Lane 4, 250 ng. (B) The effect of plasmid template on PCR was performed in a 20 µl reaction system. Lane M, λ EcoT14 I marker; Lane 1, 10 ng; Lane 2, 20 ng; Lane 3, 30 ng; Lane 4, 40 ng. (C) The effect of DNA ligase amounts on PCR was performed in a 20 µl reaction system. Lane M, λ EcoT14 I marker; line 1, 0.02 µg/µl ligase; Lane 2, 0.06 µg/µl ligase; Lane 3, 0.1 µg/µl ligase; Lane 4, 0.2 µg/µl ligase; Lane 5, 0.3 µg/µl ligase.

DETAILED DESCRIPTION OF THE INVENTION

What follows is a detailed description of specific embodiments of the invention in which the invention may be practiced. Reference will be made to the attached drawings, and the information included in the drawings is part of this detailed description. The specific embodiments of the invention, which will be described herein, are presented for exemplification purposes, and not for limitation purposes. It should be understood that structural and/or logical modifications could be made by someone of ordinary skills in the art without departing from the scope of the present invention. Therefore, the scope of the present invention is defined only by the accompanying claims and their equivalents.

The present invention discloses, in one embodiment, a method of constructing a random mutagenesis library, wherein the method comprises 1) providing a first expression vector comprising a target polynucleotide fragment, wherein the first expression vector comprises a vector portion and a target portion, wherein the vector portion comprises a first selection marker, and a first region and a second region flanking the first selection marker, wherein the target portion comprises a target polynucleotide capable of being expressed; 2) providing a pair of Vector-primers that are complementary to the vector portion of the first expression vector at least in the first and second regions, wherein the Vector-primers comprise a second selection marker flanked by the first and second regions, and wherein the Vector-primers allow PCR amplification of the target polynucleotide; and 3) performing a PCR reaction using the first expression vector as the template with the Vector-primers under error-prone PCR conditions in the presence of a thermostable DNA ligase, to generate a second expression vector which comprises the second selection marker and a mutated target polynucleotide.

As will be recognized by those skilled in the art, any expression vector suitable for cloning purpose can be used for the method of the present invention. Preferably, the expression vector is one suitable for expression in a *E. coli* cell. In a preferred embodiment, the expression vector is pHsh (17).

Figure 2:
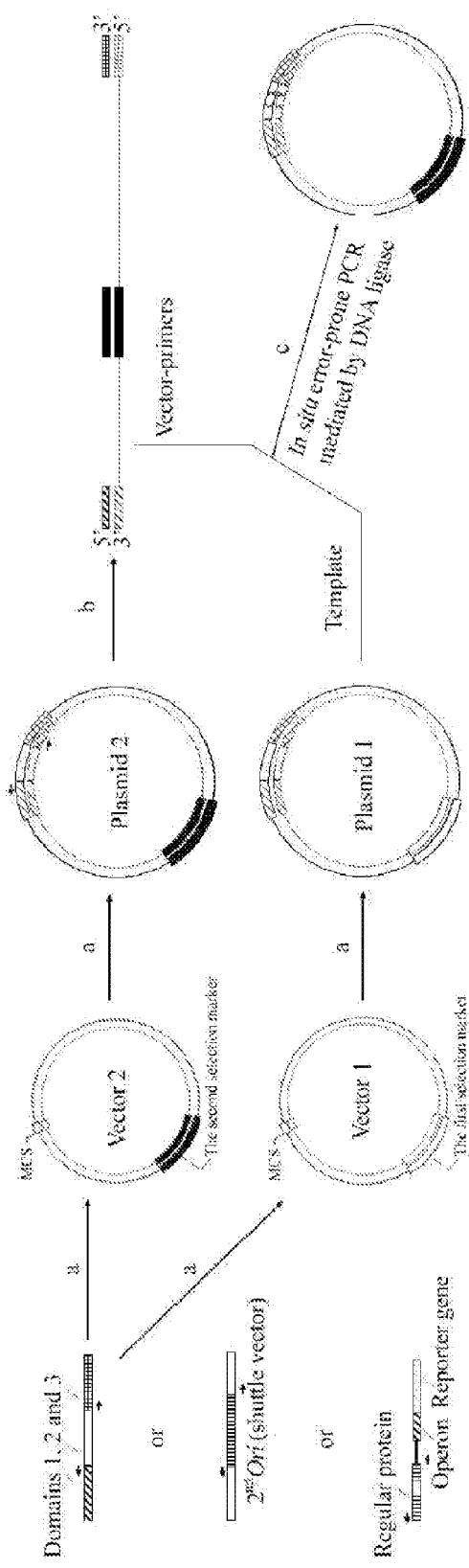
FIG. 2 illustrates a variation of the method shown in FIG. 1. In this variation, the target sequence is independently cloned into Vector 2 as well as Vector 1. Plasmid 2, which is Vector 2 containing the target sequence, is used to prepare the Vector-primers. The placement of the PCR primers (shown as short solid arrows) can be varied such that the region of the target nucleotide sequence that is desired to be mutated can be precisely selected. In other words, through the placement of the PCR primers in the production of the vector-primers, the region that is desired to be mutated under error-prone PCR conditions can be isolated, while the rest of the target nucleotide sequence are left un-mutated. This method can be used, for example, to only mutate one region of the target sequence, leaving the other regions un-mutated.
Figure 3:
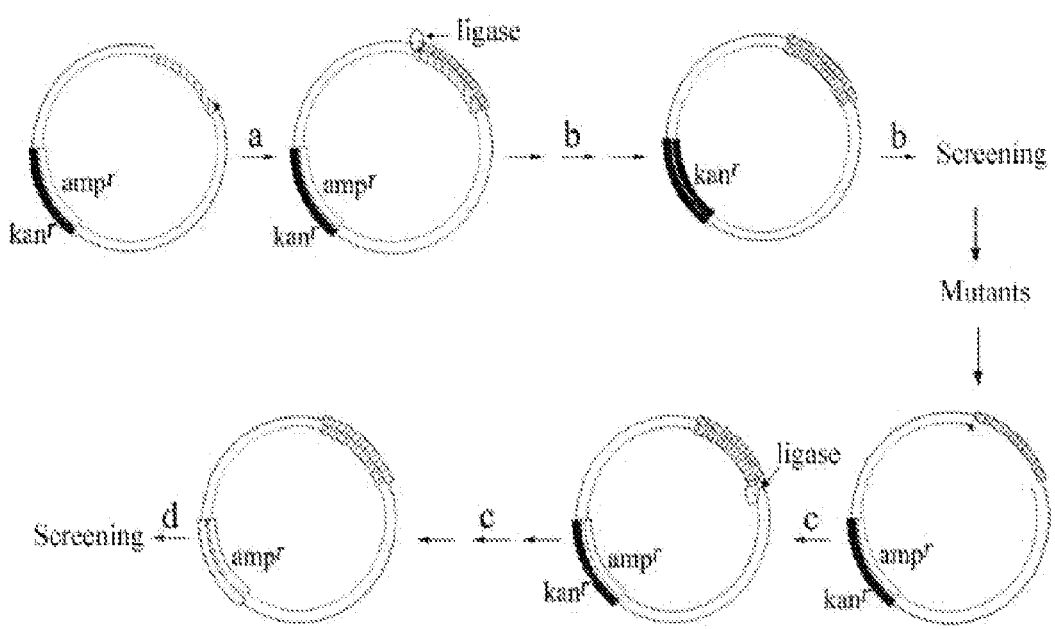

Similarly, the target polynucleotide suitable for the present invention can be any coding sequence, which is desired to be mutated and/or studied for mutagenesis. This can be a full-length coding sequence for a protein, or a RNA or regulatory sequence (e.g. see FIG. 2). One of ordinary skills in the art will be able to select a target sequence with a suitable length.

Selection markers suitable for the present invention are numerous, known and readily available to those skilled in the art. In one embodiment, the selection marker may be a polynucleotide sequence coding for resistance to an antibiotic. In another embodiment, the first selection marker encodes resistance to one antibiotic, while the second selection marker encodes resistance to a second antibiotic.

Unique to the present invention is the use of a pair of ultra-long PCR primers, hereinafter referred to as "Vector-primers". These primers are reverse complements of each other, and when not denatured are double-stranded. This double stranded fragment comprises a coding region for a selection marker (which, if an antibiotic resistance gene, will be about 1 kb in length). The two ends that flank this central region should be at least about 50 base long, and be completely complementary to the corresponding regions flanking the selection marker coding sequence of the first expression vector. When denatured, each strand of this double-stranded Vector-primers fragment anneals to the corresponding strand of the first expression vector, allowing PCR amplification of the target sequence region on the first expression vector. The PCR amplification products, when re-natured, are able to form a circular, double-stranded expression vector, with a nick on the newly amplified strand. This nick is repaired by the thermostable DNA ligase, completing the synthesis An ordinarily skilled person will readily recognize that a lot of flexibility exists in the design of the Vector-primers, so long as certain guidelines are followed. For example, overall length; minimum of complementary 3'- and 5'-flanking regions.

According to an embodiment of the present invention, the Vector-primers can be synthesized by conventional PCR. Specifically, a pair of conventional PCR primers can be designed to amply the corresponding region of an expression vector, that comprises the central, selection marker encoding region, as well as the two flanking regions. The resultant double-stranded PCR products can be used as the Vector-primers. Preferably, a high-fidelity thermostable DNA polymerase is used for the PCR synthesis of Vector-primers. Preferably, the thermostable DNA polymerase does not produce an "A-T overhang" such TAQ DNA polymerase. Suitable thermostable DNA polymerases include Pfu, and Pyrobest DNA polymerases . . . .

The amplification of the target polynucleotide sequence, hence the generation of the site-directed mutagenesis library, should be conduced with error-prone PCR. Error-prone PCR is well-known to those ordinarily skilled in the art. The fidelity of the DNA polymerase is a key factor in the error rates of the PCR amplification. For example, Taq DNA polymerase is known to have higher error rates compared to other thermostable DNA polymerases, such as Pfu. PCR conditions, as well as adjustment thereof for manipulating the degree of fidelity of the DNA polymerase used for PCR amplification, are also well-known in the art. See e.g. (16 AND 27). Specifically, the error-rates can be conveniently adjusted by modifying the concentration of $Mn^{2+}$ and $Mg^{2+}$ concentrations, as well as relative ratio of the dNTPs concentrations (i.e. "unbalanced dNTPs concentrations).

Many thermostable DNA ligases are known and readily available to those skilled in the art for error-prone PCR. Some of these ligases are provided in references no. 16 and 18, which are specifically incorporated herein by reference.

In another embodiment, the method of the present invention, the first expression vector has been confirmed to express the target polynucleotide.

It is readily recognized that the PCR reaction in step 3) above produces a circular vector with a nick, when the elongating 3'-end of the Vector-primers reaches its own 5'-end. This nick is ligated by the DNA ligase The amplified product may be easily selected based on the second selection marker. In one embodiment, selection is effected by transforming the PCR products, or second expression vector, into a suitable host cell, which is further cultured to allow the second antibiotic gene to be expressed. The process eliminates vectors that contain only the first section marker, hence are not mutated. In one embodiment, the first and second selection markers are two different antibiotic resistance genes, and the selection can be easily done via the use of two different culture media containing a corresponding antibiotic.

Further provided is a kit that comprises in a contaner, an expression vector comprising a first selection marker, and a vector-primer which comprises a second selection marker flanked by a first and second regions which first and second regions are complementary to the corresponding regions of the first selection marker of the expression vector.

Preferably, the kit of the present invention further comprises a thermostable DNA ligase. Preferably, this thermostable DNA ligase is the ligase from *Thermotoga maritima*.

In prior art methods of constructing random mutagenesis libraries, mutant DNA fragments must be digested and inserted into vectors to obtain a mutation library. Low efficiency of ligation in the post-PCR cloning process is a common problem, and the library is often plagued with unwanted plasmids that have no inserts or multiple inserts (19). This problem of ragged ends of PCR products is solved by the present invention with the use of a DNA ligase. Furthermore, thermostable DNA ligase repairs the nicks, forming a circular plasmid, and avoiding a digestion step.

The method of the present invention also substantially eliminates background transformants (i.e., those without the insert or target sequence), also a nuisance in previous approaches as they waste screening effort and decrease the diversity of the transformant library (20). In traditional methods, the background level of transformants obtained from the ligation of a vector alone must be quantified as a control. PCR products mixture must be digested by a dam-methylated DNA specific restriction enzyme, Dpn I, to eliminate the template plasmid (11, 21). In the method of the present invention, the Vector-primers contain a selection marker, e.g. a resistance gene, which greatly facilitates screening. Another advantage of the method of the present invention by using the Vector-primers to amplify whole plasmid is that no further treatment is needed for the PCR products, which can be directly transformed into host cells, e.g. competent *E. coli* cells, wherein the transformants are selected by the second selection marker, e.g. were onto LB plates containing appropriate antibiotics, to yield a library. Transformants containing only the template plasmid were removed efficiently. For example, a template plasmid pHsh-xynA1 contains ampicillin resistance gene, while the newly synthesized plasmid contains a kanamycin resistance gene. When transformants were selected in LB agar plates containing kanamycin antibiotic, only newly synthesized plasmids can grow. Moreover, the Vector-primers are universal for variable-length DNA fragments. By using these primers, variable-length DNA fragments which were cloned into the expression plasmid pHsh can create random mutagenesis libraries using this method. For example, when the cellulase gene from *T. maritima* was inserted into expression vector pHsh, a random mutagenesis library of the cellulase gene can be created.

Figure 1:
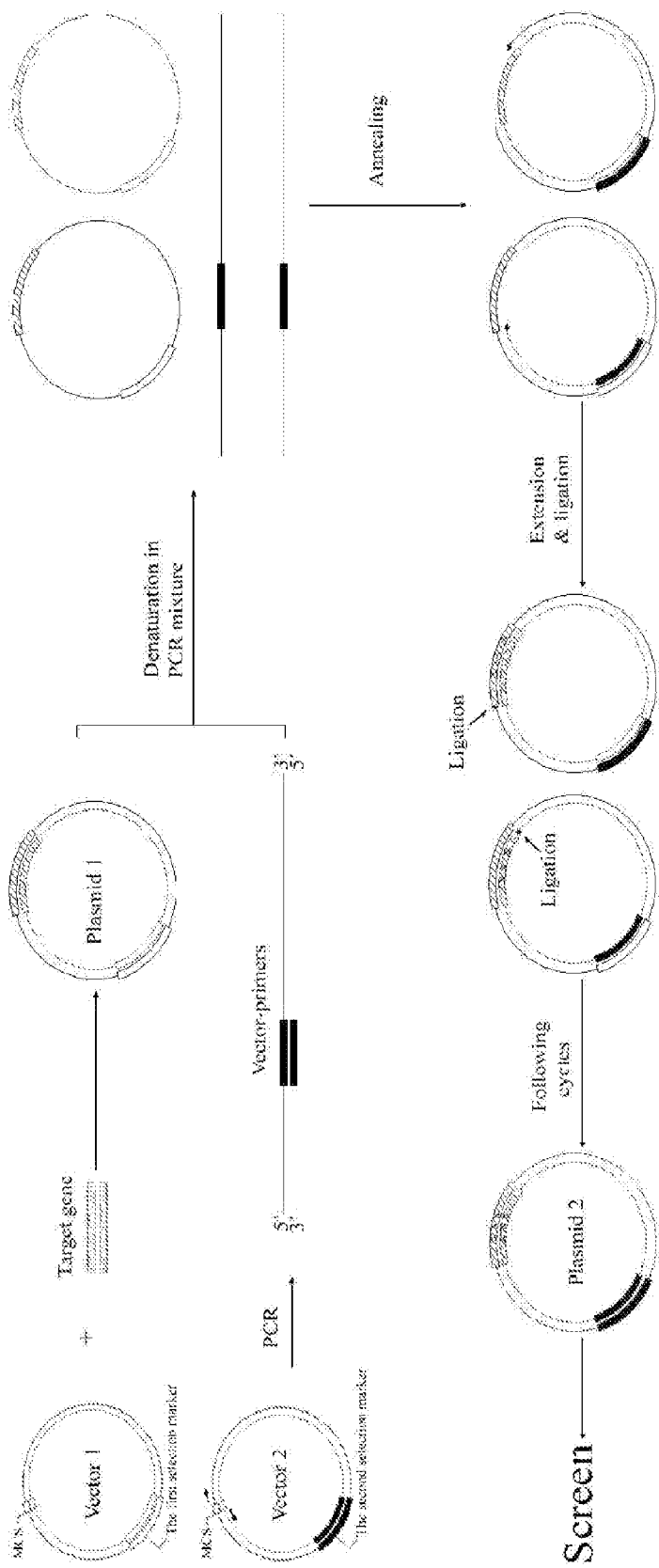
FIG. 1 is an outline of a method for creating random mutagenesis libraries according to the present invention. A target sequence is cloned into a First Vector which comprises a First Selection Marker; the cloning result is referred to as Plasmid I. A Second Vector, which comprises a second selection marker different from the first selection marker, is amplified using a pair of PCR primers (solid short arrows) designed to amplify all or almost all of the entire Second Vector, The products of this amplification are referred to as the Vector-primers. These vector-primers are used to PCR amplify the Plasmid I comprising the target polynucleotide sequence using a Vector-primers under error-prone conditions. The resultant PCR products comprise a mutated target region, and is annealed to the template Plasmid I, forming a double-stranded circular structure having a nick, with a non-annealed region where the first and second selection markers are where the sequences are not complementary. The thermally stably DNA ligase repairs the nick. Subsequent PCR cycles will produce a library of completely circular, nick-free plasmid that comprises both the second selection marker and a mutated target region. These steps are illustrated in detail as steps of denaturing, annealing, extension and nick-ligation, and subsequent PCR cycles. These nick-free plasmids will be transformed into suitable host cells, which are selected based on the second selection marker. The mutated target sequences are then expressed, followed by selection of mutants with desired mutation/directional evolution. Optionally, this step is repeated, wherein a second pair of Vector-primers, comprising a third selection marker, are used to amplify the plasmid that is the result of the first mutagenesis and selection. The third selection marker differs from the second selection marker, but may be the same as or different from the first selection marker.

In this experiment, the Vector-primers were amplified by Pyrobest DNA polymerase or Pfu DNA polymerase. Another set of primers (containing ampicillin resistance gene) can be prepared by the same method using template plasmid pHsh-amp (GenBank no: FJ571619). When the plasmid containing ampicillin resistance gene was used as template, primers containing kanamycin resistance gene were used to perform PCR. While the plasmid containing kanamycin resistance gene was used as template, linear DNA fragments containing ampicillin resistance gene can be selected to perform next PCR (FIG. 1).

Adjustment of $Mn^{2+}$ concentration is a definitive factor for the random mutagenesis (21). In this method the $Mn^{2+}$ concentration can affect not only the activity of the DNA ligase (16), but the error-rates of error-prone PCR as well. The effects of $Mn^{2+}$ concentration were examined on the random mutagenesis of the target gene using this error-prone PCR (Table 1). The products of circular plasmids increased with increasing the $Mn^{2+}$ concentration in PCR.

In conclusion, thermostable DNA ligase mediated error-phone PCR effectively created random mutagenesis libraries, and was successfully employed to improved enzyme products. The presented here lave advantages that include: (i) random mutagenesis libraries can be created by one-step error-prone PCR. (ii) variable-length DNA fragments can be used as mutation target, and there is no length limitation on the mutation target gene; (iii) no is needed for the PCR products, which can be directly transformed into competent *E. coli* cells, and the transformants can be directly screened using an appropriate antibiotics; and (iv) the accumulation of mutations can be obtained.

EXAMPLES

Materials and Methods

Bacterial Strains, Plasmids and Growth Media

*Thermotoga maritima* (ATCC43589) was grown anaerobically at 80° C. in a medium as described (22). *Escherichia coli* BL21(DE3) was used as hosts for the expression of the cellulase gene from *T. maritima*. *E. coli* Cells were cultured in Luria-Bertani (LB) medium which contained (per liter): 10 g Tryptone, 5 g yeast extract, 5 g NaCl, pH 7 and supplemented with 100 µg ampicillin $ml^{-1}$.

Preparation of the Vector-Primers

Two PCR primers 5'-pCCTCCATGGGTATATCTCCTT-3' (SEQ ID NO: 1) and 5'-pAAGCTTGAAGGCCGCTTC-CGA-3' (SEQ ID NO: 2) were used. The plasmid pHsh-kan (GenBank accession no. FJ571621) was used as template. PCR was performed in 50 µl of reaction solution containing 1.25 U Pyrobest DNA polymerase (TaKaRa Bio, Inc., Japan). A PCR amplification of 30 cycles was carried out in a 50 µl reaction system. Each cycle consisted of heating at 94° C. for 40 s, 62° C. for 40 s and 72° C. for 2 min 30 s. The resultant double-stranded PCR product is used as the Vector-primers for the ligase mediated error-prone PCR.

Thermostable DNA Ligase Mediated Error-Prone PCR of Whole Plasmid

Error-prone PCR was performed in 20 µl of reaction solution containing 30 ng plasmid pHsh-xynA1 (23) as the template, 0.5 U Taq DNA polymerase (TaKaRa Bio, Inc., Japan), 0.1 µg/µl thermostable DNA ligase (16), 200 ng Vector-primers, 0.2 mM each deoxynucleotide Triphosphate, 2.0 mM $MgCl_2$, 0.5 mM $MnCl_2$ and 0.5 mM $NAD^+$. Each cycle consisted of heating at 94° C. for 1 min, 72° C. for 1.5 min and 60° C. for 2 min.

Construction of Plasmids pHsh-celA and pHsh-CelB

The endoglucanase gene CelA was amplified from the genome of *T. maritima*. PCR amplification was carried out using the following primers 5'-CTGTGGTACTGATGACAAAACCGGGAACATC-3' (SEQ ID NO: 3) and 5'-GGGAAGCTTTCATTCTCTCACCTCCAGATC-3' (SEQ ID NO: 4). PCR products were purified using the QIAquick PCR purification kit and followed by digestion with corresponding restriction enzymes. The digested PCR products were ligated to pHsh (24) at Stu I/Hind III sites.

The endoglucanase gene CelB was amplified from the genome of *T. maritima*. PCR amplification was carried out using the following primers 5'-CTAGCGTTGGTGCAACGGAC-3' (SEQ ID NO: 5) and 5'-GGGCTCGAGTTATTTTACAACTTCGACAG-3' (SEQ ID NO: 6). PCR products were purified using the QIAquick PCR purification kit and followed by digestion with corresponding restriction enzymes. The digested PCR products were ligated to pHsh at Stu I/Xho I sites.

Construction and Screening of Xylanase Mutant Library

The error-prone PCR was performed in 20 µl of reaction solution containing 30 ng plasmid pHsh-xynA1 as template, 0.5 U Taq DNA polymerase (TaKaRa, P.R. China), 0.1 µg DNA ligase, 200 ng Vector-primers, 0.2 mM each deoxynucleotide Triphosphate, 2.0 mM $MgCl_2$, 0.1 mM $MnCl_2$ and 0.5 mM $NAD^+$. Each cycle consisted of heating at 94° C. for 1 min, 72° C. for 1.5 min and 60° C. for 2 min.

A facilitated screening, carried out on xylan-LB solid agar, relies on substrate solubilization followed by an enzymatic reaction that gives rise to a zone of identity. Transformants were overlaid with 2% xylan in solid LB and then incubated at 30° C., then up-shift of temperature to 42° C. Positive clones were identified by a zone of clearing around xylanase-expressing clones.

Construction and Screening of Cellulase Mutant Library

Error-prone PCR was performed by using pHsh-CelA or pHsh-CelB as template in the presence of thermostable DNA ligase (16). A 20 µl of reaction mixture contained 200 ng Vector-primers, 2.0 mM $MgCl_2$, 0.2 mM dNTPs each, 0.1 mM $MnCl_2$, and 0.5 U Taq DNA polymerase (TaKaRa, P.R. China) and 0.1 µg thermostable DNA ligase. DNA amplification and ligation were carried out in 15 cycles of 94° C., 1 min, 72° C., 1.5 min, and 60° C., 2 min, and a final incubation at 60° C. for 10 min, The PCR products were transformed into *E. coli* by electroporation, and mutants were screened on the plates containing 2% CMC and kanamycin (50 mg $ml^{-1}$).

Cellulase Activity Assay

Endoglucanase activity was determined by the 4-hydroxybenzoic acid hydrazide method (25). CMC (Sigma) was used as the substrate. The reaction mixture comprised of 100 µl 0.5% (w/v) CMC in water, 90 µl phosphate buffer (50 mM, pH 6.0) and 10 µl properly diluted enzyme. The reaction was conducted at 90° C. for 10 min, and stopped when 600 µl of 4-hydroxybenzoic acid hydrazide solution added into the reaction mixture. The reducing sugar was determined by reading the absorbance at 410 nm after the test tubes were incubated for 10 min in boiling water bath and cooled down on ice. One unit of endoglucanase activity was defined as the amount of enzyme releasing 1 µmol reducing sugar per min.

Results

Outline of this Method to Create Random Mutagenesis Libraries

The method of the present invention for creating random mutagenesis libraries was depicted in FIG. 1. Random mutagenesis libraries were created by error-prone PCR using whole plasmid as template. In the error-prone PCR system, the plasmid pHsh-xynA1 was used as the template, a 5'-phosphated vector-primer used as the novel primer, which comprises a kanamycin resistance gene. The vector-primer is annealed to the template plasmid except for the region of the resistance gene. Random mutations were introduced during error-prone PCR by modifications of PCR reaction conditions for the Taq DNA polymerase. The PCR reactions generate nicked circular plasmids, and a thermostable DNA ligase repaired the "nicks", resulting in a circular plasmid. The ligated circular plasmid served as template in subsequent cycles. PCR products were transformed into *E. coli* and the transformants were spread onto LB plates containing 50 µg kanamycin $ml^{-1}$.

TABLE 1

Effects of $Mn^{2+}$ concentration and cycles number on frequency of null mutants

| | Frequency of the null mutant clones (%) |
|---|---|
| $Mn^{2+}$ concentration (mM) [a] | |
| 0 | 8.3 |
| 0.1 | 59.4 |
| 0.3 | 78.0 |
| 0.5 | 87.5 |
| Number of cycles [b] | |
| 15 | 58.5 |
| 25 | 83.3 |

[a] 15 PCR cycles at various $Mn^{2+}$ concentration.
[b] 0.1 mM $Mn^{2+}$ concentration with various PCR cycles.

PCR Results in the Presence of Thermostable DNA Ligase

The PCR process in this experiment used a repetitive series of the three fundamental steps that defines one PCR cycle: double-stranded DNA template denaturation at 94° C., annealing and enzymatic extension of primers at 72° C., ligation of the nicked circular plasmid at 60° C. to produce circular plasmid as templates in subsequent cycles.

The error-prone PCR was performed in 20 µl of reaction solution. Plasmid pHsh-xynA1 was used as template. The Vector-primers, thermostable DNA ligase and plasmid template were mixed to run error-prone PCR. PCR products were electrophoresed on 1.0% agarose gel as shown in FIG. 4.

Target PCR products can be achieved by using Taq DNA polymerase in the presence of DNA ligase in this PCR reaction system. Because the DNA ligase from *T. maritima* could not ligate blunt-end DNA (16), the 5'-phosphated Vector-primers cannot be ligated together into dimers and trimers, or self-ligate.

Optimization of PCR Reaction

Because the error-prone PCR was performed using a high annealing temperature, it can also easily be performed with a two-temperature cycle consisting of denaturation and annealing/extension.

In order to optimize the PCR reaction, various ligation time at 60° C., annealing and extension time at 72° C. were performed. The products of circular plasmids increased with increased ligation time (FIG. 5A). When pHsh-xynA1 was used as template, annealing and extension time at 72° C. was 2 min (FIG. 5B).

The production yield of the final products comparatively increased with increasing the amounts of Vector-primers and plasmid template (FIGS. 6A&6B). Thermostable DNA ligase played an important role in the PCR reaction. The yield of the final products increased with increased amounts of DNA ligase (FIG. 6C). During the PCR process, the activity of DNA ligase would decrease with increased PCR amplification cycles. When the amount of DNA ligase or time of ligation was decreased, not all of the newly synthesized nicked circular plasmid can be ligated, and some linearized DNA fragments were generated (FIG. 6C). The relative abundance of DNA ligase is necessary for this PCR reaction. When these 5 factors (Ligation time, annealing and extension time, Vector-primers, plasmid template and DNA ligase) were optimized, the best results could be achieved. Under these conditions, more than $1 \times 10^5$ transformants can be obtained by using standard $E.\ coli$ competent cells ($10^7$/μg of pUC 18).

Effects of the $Mn^{2+}$ Concentration and the Number of Cycles on the Frequency of Null Mutant Clones Random mutagenesis libraries of xylanase were created using this method. At the initial screening using xylan-LB solid agar, positive clones were identified by a zone of clearing around xylanase-expressing clones. In previous experiments, we have shown that $Mn^{2+}$ concentration affected the activity of the DNA ligase from $T.\ maritima$ (16). Effects of $Mn^{2+}$ concentration and the number of cycles on the frequency of null mutant clones were studied. The frequency of inducing the null mutants (mutants that lost the xylanase activity) increased with increasing $Mn^{2+}$ concentration (Table 1). Moreover, the effects of the number of cycles on the error-rates were studied (Table 1). Both the amount of products and the error-rates increased with increasing number of cycles.

Random Mutagenesis Library Creation of Cellulase Gene

In order to create a random mutagenesis library of cellulase gene using this method, error-prone PCR was performed using pHsh-CelB as template containing Vector-primers, Thermostable DNA ligase and Taq DNA polymerase. PCR products were transformed into competent $E.\ coli$ cells. Template plasmid contains an ampicillin resistance gene, while newly synthesized plasmid contains a kanamycin resistance gene, so the transformants can be selected on agar plates containing appropriate antibiotics to eliminate the background of template plasmids.

Approximately 2,500 clones were screened. At the initial screening using CMC-LB solid agar, positive clones were identified by a zone of clearing around CMC-expressing clones. A mutant ($E.\ coli$ containing pHsh-CelB-ml) was finally chosen for further characterization. Sequence analysis of the mutant showed a point alteration at condon 61 (CAT→CTT; His-61 to Leu-61). The mutant was further cultured at 30° C. in LB medium, and overexpression of the endoglucanase gene was induced at 42° C. for 8 h at $OD_{600}$ about 0.6. The CelB-ml expressed from the mutant was increased from 0.89 to 3.88 U/ml.

Random mutagenesis libraries of gene CelA was created using this method. Approximately 2,000 clones were screened. A mutant was finally chosen and increased from 2.9 to 4.4 U/ml. The mutated endoglucanase gene, designated as CelA-ml, was sequenced, and 5 mutation points were found. Sequence results showed that F102 residue was substituted by S that resulted from the change in the DNA sequence from TTC to TCC, and L203 (CTT to CTA), L222 (CTT to CTC), G234 (GGA to GGT), and A241 (GCA to GCT) residue was not substituted where base change does not alter the coded amino acid.

The thermostable DNA ligase from $T.\ maritima$ has high thermal stability, and the enzyme had a half-life of over 30 min at 95° C. (16). The DNA ligase exhibited activity on DNA fragments with cohesive termini, and no activity were detected on blunt-end DNA. The ligase reaction required $NAD^+$, and a divalent cation including $Mg^{2+}$, $Mn^{2+}$ or $Ca^{2+}$ (16).

In conventional methods, when PCR samples were amplified by the Taq DNA polymerase, PCR products will often have single base overhangs at the 3' end of each polymerized strand, so it is necessary to remove extra nucleotides at the 3' end of the products to avoid unintended consequences (26). A mutated gene fragment, which was prepared with error-prone PCR or other methods, must be digested with appropriate restriction enzymes and ligated into an expression vector (11, 27-29).

Although specific embodiments have been illustrated and described herein for the purpose of disclosing the preferred embodiments, someone of ordinary skills in the art will easily detect alternate embodiments and/or equivalent variations, which may be capable of achieving the same results, and which may be substituted for the specific embodiments illustrated and described herein without departing from the scope of the present invention. Therefore, the scope of this application is intended to cover alternate embodiments and/or equivalent variations of the specific embodiments illustrated and/or described herein. Hence, the scope of the present invention is defined only by the accompanying claims and their equivalents.

REFERENCES

1. Chirumamilla, R. R., Muralidhar, R., Marchant, R. and Nigam, P. (2001) Improving the quality of industrially important enzymes by directed evolution. *Mol. Cell. Biochem.*, 224, 159-168.
2. Cherry, J. R. and Fidantsef, A. L. (2003) Directed evolution of industrial enzymes: an update. *Curr. Opin. Biotechnol.*, 14, 438-443.
3. Eijsink, V. G. H., Gaseidnes, S., Borchert, T. V. and van den, B. (2005) Directed evolution of enzyme stability. *Biomol. Eng*, 22, 21-30.
4. Yuan, L., Kurek, I., English, J. and Keenan, R. (2005) Laboratory-directed protein evolution. *Microbiol. Mol. Biol. Rev.*, 69, 373-392.
5. Olsen, M., Iverson, B. and Georgiou, G. (2000) High-throughput screening of enzyme libraries. *Curr. Opin. Biotechnol.*, 11, 331-337.
6. Otten, L. G. and Quax, W. J. (2005) Directed evolution: selecting today's biocatalysts. *Biomol. Eng*, 22, 1-9.
7. Lutz, S. and Patrick, W. M. (2004) Novel methods for directed evolution of enzymes: quality, not quantity. *Curr. Opin. Biotechnol.*, 15, 291-297.
8. Ling, M. M. and Robinson, B. H. (1997) Approaches to DNA Mutagenesis: An Overview. *Anal. Biochem.*, 254, 157-178.
9. Cadwell, R. C. and Joyce, G. F. (1992) Randomization of genes by PCR mutagenesis. *PCR methods and applications*, 2, 28-33.

10. Leung, D. W., Chen, E., and Goeddel, D. V. (1989) A method for random mutagenesis of a defined DNA segment using a modified polymerase chain reaction. *Technique*, 1, 11-15.

11. Miyazaki, K. and Takenouchi, M. (2002) Creating random mutagenesis libraries using megaprimer PCR of whole plasmid. *Biotechniques*, 33, 1033-1038.

12. Sarkar, G. and Sommer, S. S. (1990) The "megaprimer" method of site-directed mutagenesis. *Biotechniques*, 8, 404-407.

13. Brons-Poulsen, J., Petersen, N. E., Horder, M. and Kristiansen, K. (1998) An improved PCR-based method for site directed mutagenesis using megaprimers. *Molecular and cellular probes*, 12, 345-348.

14. Tyagi, R., Lai, R. and Duggleby, R. G. (2004) A new approach to 'megaprimer' polymerase chain reaction mutagenesis without an intermediate gel purification step. *Bmc Biotechnology*, 4, 2-7.

15. Kammann, M., Laufs, J., Schell, J. and Gronenborn, B. (1989) Rapid insertional mutagenesis of DNA by polymerase chain reaction (PCR). *Nucleic Acids Res.*, 17, 5404.

16. Le Y, Peng J, Pei J, Li H, Duan Z, Shao W. (2009) Properties of an $NAD^+$-dependent DNA ligase from the hyperthermophile *Thermotoga maritima* and its application in PCR amplification of long DNA fragments. *Enzyme Microb. Technol.*, 2010, 46, 113-117.

17. Vieira, J., and Messing, J. (1982) The pUC plasmids, an M13mp7-derived system for insertion mutagenesis and sequencing with synthetic universal primers. Gene, 19: 259-268.

18. Takahashi, M., Yamaguchi, E., Uchida, T. (1984) Thermophilic DNA ligase. Purification and properties of the enzyme from *Thermus thermophilus* HB8. J Biol Chem, 259:10041-10047.

19. Shen, B. (2002) PCR approaches to DNA mutagenesis and recombination. An overview. *Methodas Mol. Biol.*, 192, 167-174.

20. Tobias, A. V. (2003) Preparing libraries in *Escherichia coli. Methods Mol. Biol.*, 231, 11-16.

21. Wei, D., Li, M., Zhang, X. and Xing, L. (2004) An improvement of the site-directed mutagenesis method by combination of megaprimer, one-side PCR and Dpn I treatment. *Anal. Biochem.*, 331, 401-403.

22. Jiang, Y., Zhou, Q., Wu, K., Li, X. Q. and Shao, W. L. (2006) A highly efficient method for liquid and solid cultivation of the anaerobic hyperthermophilic eubacterium *Thermotoga maritima. FEMS Microbiol. Lett.*, 259, 254-259.

23. Yin, E., Le, Y., Pei, J., Shao, W. and Yang, Q. (2008) High-level expression of the xylanase from *Thermomyces lanuginosus* in *Escherichia coli. World J. Microbiol. Biotechnol.*, 24, 275-280.

24. Shao, W., Wu, H. and Pei, J. (2006) A plasmid vector controlled by the Sigma 32 factor of *Escherichia coli* and its use for the expression of heterologous protein. International Patent. PCT WO2006/002574A1.

25. Lever, M. (1972) A new reaction for colorimetric determination of carbohydrates. *Anal. Biochem.*, 47, 273-279.

26. Hu, G. (1993) DNA polymerase-catalyzed addition of nontemplated extra nucleotides to the 3' end of a DNA fragment. *DNA and cell biology*, 12, 763-770.

27. Nakaniwa, T., Tada, T., Takao, M., Sakai, T. and Nishimur, k. (2004) An in vitro evaluation of a thermostable pectate lyase by using error-prone PCR. *Journal of Molecular Catalysis B: Enzymatic*, 27, 127-131.

28. Zhang, J. H., Dawes, G. and Stemmer, W. P. C. (1997) Directed evolution of a fucosidase from a galactosidase by DNA shuffling and screening. *Proc. Natl. Acad. Sci. USA*, 94, 4504-4509.

29. Kim M.-S. and Lei, X. G. (2008) Enhancing thermostability of *Escherichia coli* phytase AppA2 by error-prone PCR. *Appl. Microbiol. Biotechnol.*, 79, 69-75.

What is claimed is:

1. A method of constructing a random mutagenesis library, comprising:
    i) providing a first expression vector comprising a target polynucleotide fragment, wherein the first expression vector comprises a vector portion and a target portion, wherein the vector portion comprises a first selection marker gene, and a first region and a second region flanking the first selection marker gene, wherein the target portion comprises a target polynucleotide capable of being expressed;
    ii) providing a pair of Vector-primers that are complementary to the vector portion of the first expression vector in the first and second regions respectively, wherein the Vector-primers comprise a second selection marker gene, and wherein the Vector-primers allow PCR amplification of the target polynucleotide; and
    iii) performing a PCR reaction using the first expression vector as the template with the Vector-primers under error-prone PCR conditions in the presence of a thermostable DNA ligase, generating a second expression vector which is circular and comprises the second selection marker gene and a mutated target polynucleotide wherein the second expression vector does not comprise the first selection marker.

2. The method according to claim 1, wherein the first expression vector has been confirmed to express the target polynucleotide.

3. The method according to claim 1, wherein the PCR reaction in step iii) produces a circular vector with a nick, and wherein the thermostable DNA ligase ligates the nick.

4. The method according to claim 1, further comprising transforming a suitable host cell with the second expression vector, and culturing the transformed host cell to allow the second selection marker gene to be expressed for selection of the second expression vector.

5. The method according to claim 3, wherein a host cell comprising the second expression vector is cultured under a condition to allow the expression of the mutated target polynucleotide.

6. The method according to claim 1, wherein the first selection marker gene is a first antibiotic resistance gene, and the second selection marker gene is a second antibiotic gene.

7. The method according to claim 5, further comprising assaying the expression product of the mutated polynucleotide to select a mutated target polynucleotide with one or more desired mutations.

8. The method according to claim 7, wherein the expression vector comprising a mutated target polynucleotide with one or more desired mutations is used as template and subject to further directed evolution.

9. The method according to claim 7, wherein the expression vector comprising a mutated target polynucleotide with one or more desired mutations is used as a template in a PCR under error-prone conditions with a second pair of Vector-primers that are complementary to the vector portion of the expression vector comprising the desired mutated polynucleotide, wherein the second pair of Vector-primers comprise a third selection marker gene, and wherein the second Vector-primers allow PCR amplification of the target polynucleotide;

the method further comprising performing a PCR reaction with the second Vector-primers under error-prone PCR conditions in the presence of a thermostable DNA ligase, and generating a third expression vector which comprises the third selection marker gene and a further mutated target polynucleotide.

10. The method according to claim 9, wherein the third selection marker is the same as the first selection marker.

11. The method according to claim 10, wherein the first selection marker gene is a first antibiotic resistance gene, and the second selection marker gene is a second antibiotic gene.

12. A method of constructing a random mutagenesis library, comprising
   i) providing a first expression vector which comprises a vector portion and a target portion, wherein the vector portion comprises a first selection marker gene, and a first region and a second region flanking the first selection marker gene, wherein the target portion comprises a target polynucleotide capable of being expressed;
   ii) providing a pair of Vector-primers that are complementary to the vector portion of the first expression vector in the first and second regions, and complementary to a portion of the target polynucleotide that is not desired to be mutated, wherein the Vector-primers comprise a second selection marker gene, and wherein the Vector-primers allow PCR amplification of the target portion that is desired to be mutated; and
   iii) performing a PCR reaction using the first expression vector as the template with the Vector-primers under error-prone PCR conditions in the presence of a thermostable DNA ligase, generating a second expression vector which comprises the second selection marker gene and a mutated target portion wherein the second expression vector does not comprise the first selection marker.

13. The method of claim 12, wherein, prior to step (i), vector-primers are prepared by: providing an expression vector comprising the target portion and the second selectable marker, wherein the expression vector is identical to the first expression vector except the second selectable marker replaces the first selectable marker and amplifying the entire vector except the portion of the target portion that desired to be mutated, wherein the amplification occurs using high fidelity PCR conditions and a pair of PCR primers designed to amplify the entire vector except the portion desired to be mutated.

14. The method according to claim 12, wherein the first expression vector expresses the target portion.

15. The method according to claim 14, wherein the second expression vector is transformed into a suitable host cell, which is further cultured to allow the second selection marker gene to be expressed for selection of the second expression vector.

16. The method according to claim 15, wherein a host cell comprising the second expression vector is cultured under a condition to allow the expression of the mutated target polynucleotide.

17. The method according to claim 16, wherein the first selection marker gene is a first antibiotic resistance gene, and the second selection marker gene is a second antibiotic gene.

18. The method according to claim 17, wherein the expression product of the mutated polynucleotide is assayed to select a mutated target polynucleotide with one or more desired mutations.

19. The method according to claim 18, wherein the expression vector comprising a mutated target polynucleotide with one or more desired mutations is used as template and subject to further directed evolution.

20. The method according to claim 19, wherein the expression vector comprising a mutated target polynucleotide with one or more desired mutations is used as a template in a PCR under error-prone conditions with a second pair of Vector-primers that are complementary to the vector portion of the expression vector comprising the desired mutated polynucleotide, wherein the second pair of Vector-primers that comprise a third selection marker gene, and wherein the second Vector-primers allow PCR amplification of the target polynucleotide; and performing a PCR reaction with the second Vector-primers under error-prone PCR conditions in the presence of a thermostable DNA ligase, generating a third expression vector which comprises the third selection marker gene and a further mutated target polynucleotide.

* * * * *